(12) United States Patent  
Piel et al.

(10) Patent No.: US 7,714,992 B2  
(45) Date of Patent: May 11, 2010

(54) EQUIPMENT AND METHOD FOR MONITORING AN IMMERSION LITHOGRAPHY DEVICE

(75) Inventors: Jean-Philippe Piel, Marly-le-Roi (FR); Jean-Louis Stehle, Colombes (FR)

(73) Assignee: Societe de Production et de Recherches Appliquees (S.O.P.R.A.), Bois-Colombes (FR)

( * ) Notice: Subject to any disclaimer, the term of this patent is extended or adjusted under 35 U.S.C. 154(b) by 263 days.

(21) Appl. No.: 11/991,613

(22) PCT Filed: Sep. 11, 2006

(86) PCT No.: PCT/FR2006/002077

§ 371 (c)(1),  
(2), (4) Date: Mar. 7, 2008

(87) PCT Pub. No.: WO2007/031630

PCT Pub. Date: Mar. 22, 2007

(65) Prior Publication Data

US 2009/0116001 A1    May 7, 2009

(30) Foreign Application Priority Data

Sep. 12, 2005  (FR) .................................. 05 09269

(51) Int. Cl.  
*G01N 21/41* (2006.01)
(52) U.S. Cl. ...................................... 356/128; 356/134
(58) Field of Classification Search .......... 356/128–137  
See application file for complete search history.

(56) References Cited

U.S. PATENT DOCUMENTS 7,196,770 B2 * 3/2007 Baselmans et al. ............ 355/53

7,643,127 B2 * 1/2010 Baselmans et al. ............ 355/53

(Continued)

FOREIGN PATENT DOCUMENTS

GB    2 141 223 A    12/1984

(Continued)

OTHER PUBLICATIONS

International Search Report, dated Jan. 22, 2007, corresponding to PCT/FR2006/002077.

(Continued)

*Primary Examiner*—Michael P Stafira  
(74) *Attorney, Agent, or Firm*—Christie, Parker & Hale, LLP

(57) ABSTRACT

The invention concerns an equipment for monitoring an immersion lithography device provided with a main light source and a projection optics for printing images on a wafer. The propagating medium extending from the projection optics to the wafer consists of a liquid (3). The equipment comprises: a chamber (51) for receiving at least part of said liquid (3), a diffraction grating (50) immersed in the chamber; a secondary light source (271) for emitting a secondary incident beam (20) towards the grating so as to obtain a diffracted beam; angle measuring members (57) capable of measuring at least one diffraction angle corresponding to a maximum intensity of an order of diffraction of the beam diffracted by the grating (500), and computing means (505) for calculating an estimate of a physical quantity concerning the refractive index of the liquid.

19 Claims, 7 Drawing Sheets

U.S. PATENT DOCUMENTS

2007/0132979 A1* 6/2007 Lof et al. .................. 355/69
2008/0252876 A1* 10/2008 Mengel et al. ............. 356/51
2009/0021709 A1* 1/2009 Nagasaka .................. 355/53

FOREIGN PATENT DOCUMENTS

WO WO 2005/013008 A2 2/2005
WO WO 2005/019935 A2 3/2005

OTHER PUBLICATIONS

Owa, et al., "Immersion lithography; its potential performance and issues," Proceedings of SPIE, vol. 5040 (2003), pp. 724-733, XP-002294500.

* cited by examiner

EQUIPMENT AND METHOD FOR MONITORING AN IMMERSION LITHOGRAPHY DEVICE

CROSS-REFERENCE TO RELATED APPLICATION

This application is a National Phase Patent Application of International Application No. PCT/FR2006/002077, filed on Sep. 11, 2006, which claims priority of French Patent Application No. 0509269, filed on Sep. 12, 2005.

FIELD OF THE INVENTION

The invention relates to an equipment and method for measuring an index of a liquid which is useful in the monitoring of an immersion lithography device, particularly for the manufacture of integrated circuits, in the micro-electronics field.

Lithography techniques are used to transcribe onto the photosensitised surface of a silicon chip patterns represented by a mask, thus making it possible to form electronic components of integrated circuits.

BACKGROUND OF THE INVENTION

In a conventional lithographic device, a light source emits a light beam that passes through an optical projection device fitted with the mask so as to project an image of this mask onto the chip. The characteristics of the image projected, notably the resolution and field depth, are chiefly linked to the exposure wavelengths and the numerical aperture of the objectives used in the optical projection device. The trend to miniaturise integrated circuits involves improving these characteristics.

One method of improvement is to use ever shorter emission wavelengths. Thus, it has been possible to progress from the use of high pressure mercury vapour lamps operating at wavelengths of about 405 nm, then 365 nm, to the use of excimer lasers operating at wavelengths of 248 nm and then 193 nm, resulting in a substantial reduction in the emission wavelengths. Going any lower, so as to achieve a wavelength of 157 nm, for example, creates problems, especially in the production of optical projection devices.

Another, additional, method of improvement sets out to increase the numerical aperture of the optical devices.

Conventionally, the propagation medium that separates the optical projection device from the lithographic device of the silicon chips is air, in which the values of the numerical aperture are limited to 1. It is possible to increase the numerical aperture still further by replacing air with a liquid having an index greater than 1, for example water or any other suitable immersion liquid. This is known as "immersion photolithography".

However, the theoretical performance of immersion photolithography is far from being achieved in practice because, at this level, there are significant variations in the properties of the optical projection device, with its immersion liquid placed between the optical projection device and the silicon chip. Thus, the quality of the image projected and/or its magnification change as a function of the different operating parameters of the lithographic device, particularly the refractive index of the liquid, the emission wavelength of the light source, the temperature of the optical projection device, ambient temperature, and the temperature of the chip.

It is desirable to be able to control the variations in these parameters, as any variation of this type causes a degradation of the integrated circuits manufactured and/or a loss of yield which rapidly becomes unacceptable. For example, the working wavelength of the light source can be controlled with a precision of the order of $5.10^{-7}$; it is possible to control the temperature of the optical projection device and ambient temperature with a precision of the order of 0.005° C.

The refractive index of the liquid still remains. Variations in this index influence the quality (resolution) of the projected image and/or its magnification. The variations in the refractive index are linked to various reasons, for example the purity of the liquid, the emission wavelengths, the temperature of the liquid and the pressure of the liquid. These variations ought to be controlled with a precision comparable to that of the wavelength of the laser of the light source.

Existing equipment and methods of monitoring are still not entirely satisfactory, even the best ("Immersion Lithography Workshop", 27 Jan. 2004, published by the NIST, National Institute of Standards and Technology).

The invention sets out to improve the situation.

SUMMARY OF INVENTION

As before, the immersion lithographic device is equipped with a main light source and an optical projection device for printing images on a chip. The propagation medium going from the optical projection device to the chip consists of a liquid. According to the invention the monitoring equipment of this device comprises:
- a chamber adapted to receive at least some of the liquid,
- a diffraction grating immersed in the chamber;
- a secondary light source capable of sending a secondary incident beam to the grating so as to obtain a diffracted beam,
- angle measuring means capable of measuring at least one diffraction angle corresponding to an intensity maximum of an order of diffraction of the beam diffracted by the grating and
- computing means adapted to calculate an estimate of a magnitude relating to the refractive index of the liquid.

The invention also proposes a method of monitoring an immersion lithographic device equipped with a main light source and an optical projection device for printing images on a chip, the propagation medium that goes from the optical projection device to the plate being made up of a liquid. The process comprises the following steps:
a) providing a chamber that accommodates at least some of the liquid (in principle all the liquid, over time),
b) sending a secondary incident beam to a diffraction grating immersed in the chamber,
c) measuring at least one diffraction angle corresponding to the intensity maximum of at least one order of diffraction of the beam diffracted by the grating, and
d) calculating an estimate of a magnitude relating to the refractive index of the liquid.

Further features and advantages of the invention will become apparent from an examination of the detailed description that follows and the attached drawings, wherein:

Annexe A contains the equations linking various optical parameters which are included in the implementation of the invention.

DESCRIPTION OF THE PREFERRED EMBODIMENTS

This annexe is set apart in the interests of clarity and to make it easier to refer to it. It forms an integral part of the description and can therefore not only serve to improve the understanding of the present invention but can also contribute to its definition, where appropriate. This is also true in every respect of the drawings.

Figure 1:
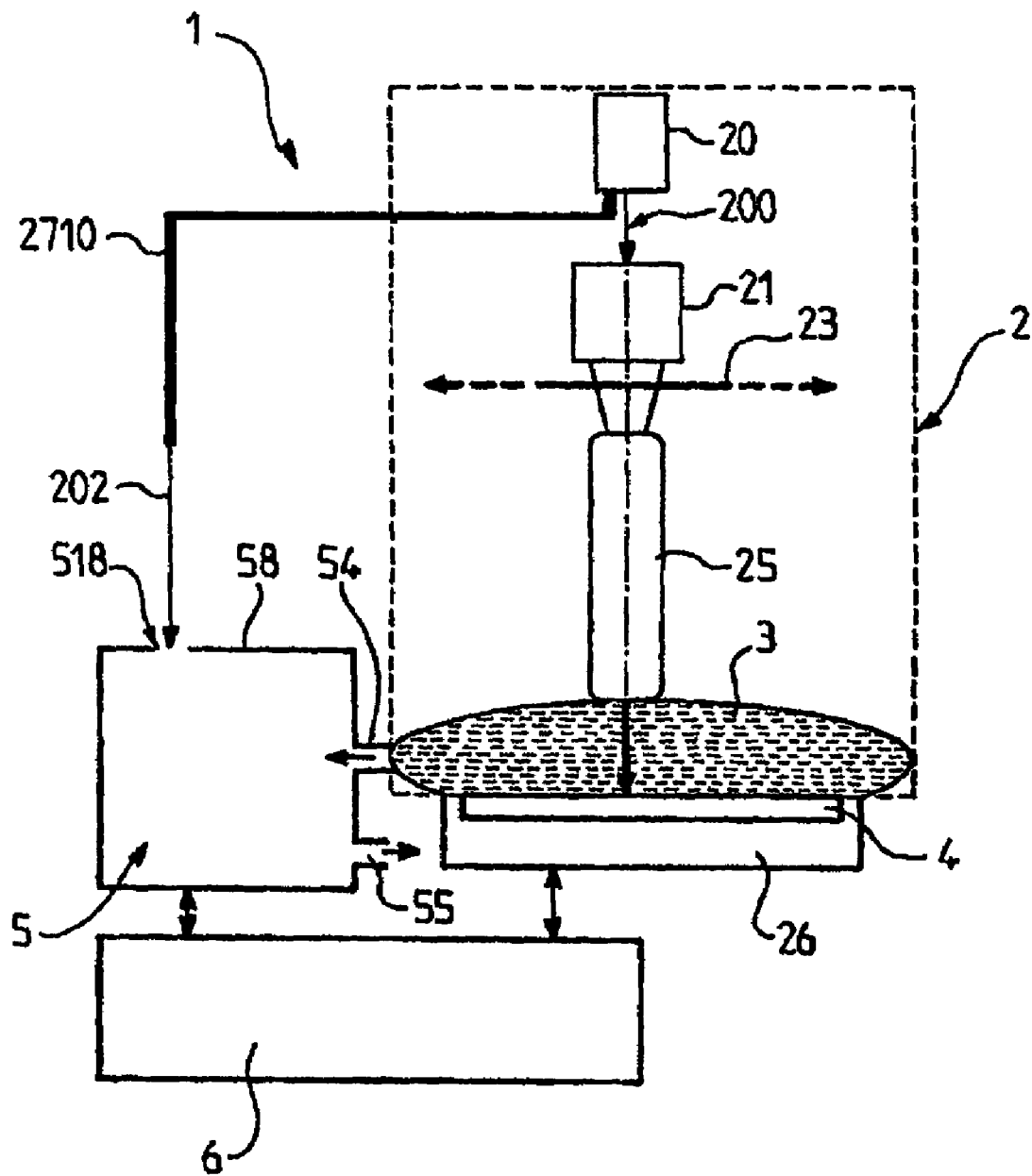
FIG. 1 is a general diagram of an installation comprising an immersion lithographic device and monitoring equipment according to the invention.

First of all, reference is made to FIG. 1 which is a general diagram of an installation 1 comprising a lithographic device 2 and its monitoring equipment 5.

The lithographic device 2 is intended to print images on a chip 4, particularly a silicon chip, the surface of which is coated with a photosensitive resin ("photoresist"). In the present description, the word "chip" chiefly relates to a chip with a surface that has been made photosensitive.

In the lithographic device 2, the propagation medium located in the vicinity of the chip 4 comprises an immersion liquid 3, such as water. The immersion liquid 3 is characterised by a refractive index N which needs to be stabilised in order to avoid variations in the characteristics of the images printed on the chip, notably their position.

The lithographic device 2 comprises, on an optical axis extending perpendicularly to the plate 4, a main light source 20, a condenser 21, a lithographic mask 23, an optical projection device 25 and the liquid 3.

The equipment 5 is intended to measure the refractive index N of the immersion liquid 3. What matters to begin with is the precision, sensitivity and faithfulness (repeatability) of this measurement. In fact, the basic idea is to discover the variations in N in order to compensate them. Moreover, a (less precise) value for N is already available, matched with a fairly narrow margin of variations. In order to control a corrective feedback of N it is sufficient to know the variations of N with great precision without necessarily knowing its absolute value with the same precision. However, it may also be necessary to know the absolute value of N with the same precision as its variations, or thereabouts, in certain cases. For these reasons the general terminology used is an "estimation" of the variations of N, or of a connected or representative magnitude, but it must be clear that this estimation may be precise or even very precise.

The light source 20 of the lithographic device 2 may be, for example, an atomic ray lamp or an excimer laser. The light source produces a main light beam 200, sent to the mask 23 of the lithographic device. The light beam has a known, stable wavelength, in particular 193 nm or 157.7 nm (owing to the precise values of rays).

The beam then passes through various optical components including the condenser 21. The beam then passes through the mask 23, the optical projection device 25, and then the liquid 3. The optical projection device 25 and the liquid 3 focus the beam on a target zone of the chip 4.

In general, the same chip is exposed several times by the same mask in order to repeat the same pattern on it (which may already be a repeat pattern on the mask). For this purpose, the chip 4 may be mounted on a bench 26 which enables the substrate to be moved precisely so as to position different target zones in the path of the beam. In practice, the relative movement of the chip and mask is of the "scanner" type rather than the earlier "stepper" type.

The interaction between the lithographic device 2 and the monitoring equipment 5 will now be described.

According to the invention, the installation comprises a secondary light source 271 capable of supplying a secondary light beam 202. In the embodiment shown in FIG. 1, a single common source forms both the main source 20 and the secondary source 271. This common source emits the main light beam 200 and the secondary beam 202. In this embodiment, a beam separator (or other sampling means) may be provided at the output of the common source to divide the beam emitted into a main beam 200 sent to the optical projection device 25 and a secondary beam 202 sent towards the equipment 5, which enables exactly the same wavelength to be achieved. The secondary beam may for example be carried by an optical fibre 2710. In FIG. 1, the main beam 200 and the secondary beam 202 are shown diagrammatically.

The secondary light source 202 may also be separate from the main light source 20, notably within an experimental framework.

The monitoring equipment 5 comprises a chamber 51, e.g. made of stainless steel, equipped with a liquid intake 54 receiving at least some of the immersion liquid 3 and a liquid outlet 55 through which the liquid leaves the chamber 51 to return to the lithographic device. Thus the liquid 3 may be continuously taken from the lithographic device to the chamber 51. Consequently, all the liquid 3 may be passed from the lithographic device to the chamber over a selected period of time.

The chamber 51 is, furthermore, provided with an aperture 518 to receive the secondary light beam 202.

The equipment 5 according to the invention makes it possible to calculate an estimate of a magnitude relating to the refractive index N of the immersion liquid 3, notably in order to monitor the variations in the refractive index N of the liquid and correct them, or correct their effects.

Figure 2:
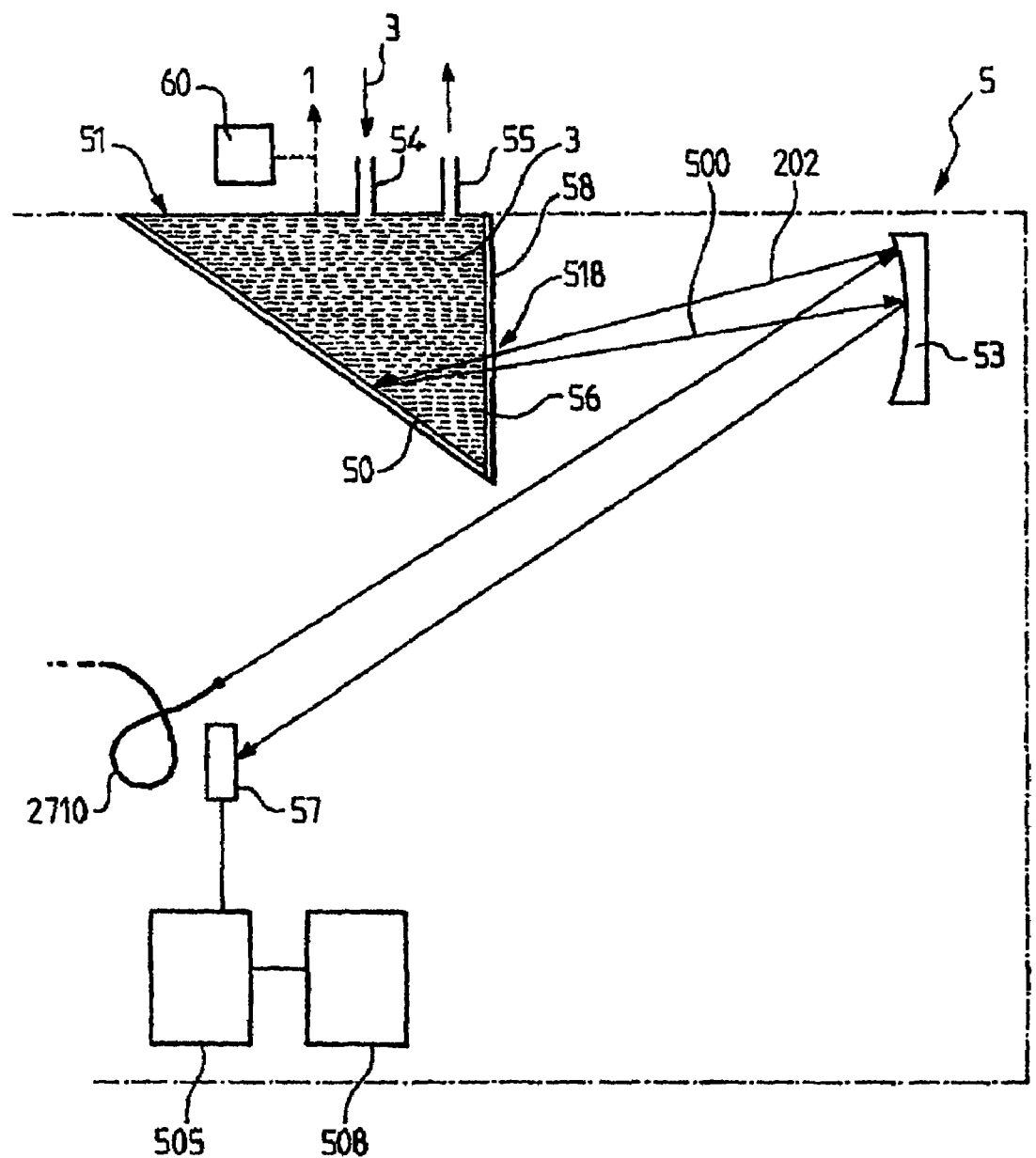
FIG. 2 is a schematic plan view of the equipment according to the invention.

FIG. 2 is a diagram showing a plan view of the equipment 5 according to the invention.

The liquid intake 54 opens into the chamber 51 so as to cause at least some of the immersion liquid 3 of the lithographic device 1 to circulate therein. The liquid leaves the chamber through the liquid outlet 55.

A diffraction grating 50 is placed inside the chamber 51 in order to diffract the incident secondary beam 202. The grating is, in particular, a reflection grating, for example an echelle grating, characterised by a number of lines per mm g.

It has been shown that the refractive index of the liquid varies as a function of temperature (by NIST, the National Institute of Standards and Technology). For example, it has been shown that the variation in the index of water is connected to variations in the temperature of the water according to a ratio substantially equal to $-10^{-4}$ per 1° C. In order to be able to monitor variations in the refractive index N due to other causes it is therefore useful to stabilise the temperature of the liquid in the chamber 51. For this, a temperature control system 60 may be provided, in known manner, to maintain a selected liquid temperature in the chamber 51. In particular the temperature of the liquid is stabilised at better than $10^{-2}$ degrees Celsius. This selected temperature is regulated jointly with the lithographic device 2, if necessary over the whole device.

The active side of the grating 50 is bathed by the liquid 3 and is positioned and arranged in the chamber so as to receive the incident secondary beam 202. The diffraction grating 50 then diffracts the secondary light beam 202, producing a plurality of beams diffracted to different degrees, at least one of which 500 is sent to angle measuring means 57.

The equipment 5 may also comprise an optical focusing device 53, in this case a collimating mirror, for focusing the diffracted light beam 500 towards the angle measuring means 57.

In the foregoing description the secondary light beam has been described as being the beam sent by the secondary source 271 to the grating 50. However, the beam emitted by the source 271 may undergo a certain number of optical phenomena before entering the chamber 51 in the form of an incident secondary beam 202. Thus, in the embodiment shown in FIG. 2, the collimating mirror 53 is also used to bring the beam emitted by the secondary source 271 into the chamber 51.

It will be noted that the incident beam and the diffracted beam (used) in this case are on the same side of the perpendicular to the diffraction grating 50 and are fairly sharply inclined to this perpendicular.

The side wall 58 is closed off by a plate 56, notably with parallel sides, which insulates the chamber 51 from the outside. A plate which is transparent to the working wavelengths will be used in particular, for example a silica plate for ultraviolet.

In the embodiment described the plate with parallel sides is arranged close to the perpendicular to the beam. When the plate is tilted in one direction the sensitivity of the estimate of the magnitude relating to the refractive index N is reduced; in the other direction the sensitivity of this value is increased by the effect of refraction of the prismatic interface between liquid/plate/air.

Figure 3:
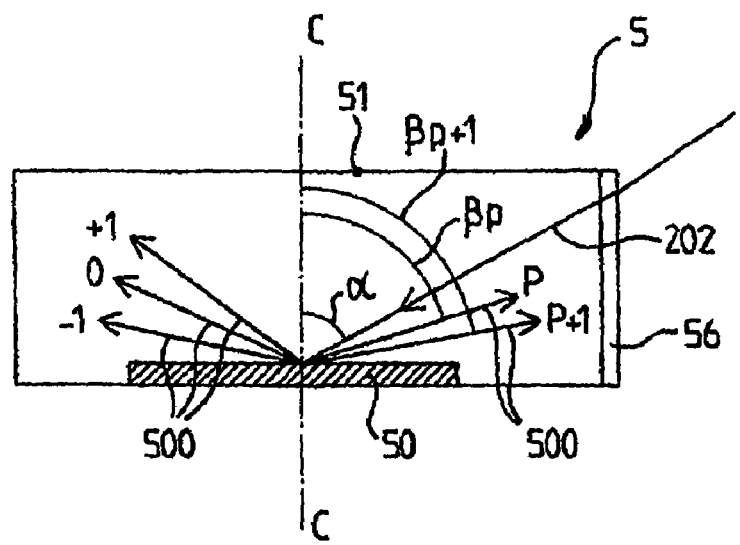
FIG. 3 is a diagram of the equipment according to the invention illustrating the diffraction of an incident light beam on the grating.

The equipment 5 further comprises computing means 505 capable of producing an estimate of a magnitude relating to the refractive index N based on the measurement of at least one diffraction angle $\beta_p$ corresponding to the maximum intensity of a diffraction order p of the diffracted beam 500, as will be seen with reference to FIG. 3.

It may be that the angle of incidence $\alpha$ formed by the incident light beam with the perpendicular CC to the grating is known in advance by design. If this is not the case, the angle measuring means 57 may also measure the angle of incidence $\alpha$ formed by the incident light beam with the perpendicular CC to the grating.

Additionally, the angle measuring means 57 may measure not only the diffraction angle $\beta_p$ but also one other angle or several other angles. This other angle may be $\beta_{p+1}$, corresponding to a diffracted beam 500 of the order (p+1).

The equipment 5 according to the invention may also interact with a monitoring device for the liquid 6 shown in FIG. 1, capable of implementing corrective actions such as an adjustment to the temperature and/or pressure of the liquid, the addition of an additive or diluant, more effective filtering or total replacement of the liquid as a function of the level of the variations in the refractive index. Alternatively or additionally, corrective actions may be taken manually by an operator. The liquid of the chamber 51 may be replaced when corrective actions are implemented.

The bases of the calculation are illustrated by the attached equations A1 to A4.

Equation A1 shows that by knowing (or measuring) the angle $\alpha$ with precision and measuring an angle $\beta_p$ with precision, it is possible to determine N. In fact, g and $\lambda$ are known with precision. Only the order p is missing. However, as the range in which N is located is known, it is possible to remove the ambiguity as to the integer p, as soon as the range of uncertainty as to N is less than the increment in the second member of A1 when p increases by 1. This increment, expressed by the formula A3, is (g. $\lambda/N_{app}$) where $N_{app}$ is the "rough" value of N which is already known.

Whatever the case may be, with $\alpha$ constant, the variations in (1/sin $\beta_p$) are proportional to the variations in N. Thus, without exactly knowing the order p it is theoretically possible to access the variations in dN/N.

This leaves the effect of the plate with parallel sides 56, which can be illustrated by the equation A4. In this equation, the parameters $n_{liq}$, $n_{plate}$, and $n_{air}$ respectively represent the liquid index, the plate index and the air index, and the parameters $i_{liq}$, $i_{plate}$ and $i_{air}$ represent the angle formed by the diffracted beam with the perpendicular to the plate 56 in the liquid medium, in the plate and in the air, respectively. This effect comprises:

a change of angle, and
a lateral offset of the beam, depending on the thickness of the plate.

Although it is theoretically neutral, this effect will complicate the measurement in practice once the measurement of the angle is carried out on bases fixed at X and Y. How to take account of this in order to achieve a precise absolute value for N will be described hereinafter.

Thus, it is possible to obtain:
at the least a value of N with very precise variations;
better still, with a very precise value of N in absolute terms.

The value of N thus calculated, or a representation thereof, can be stored in a memory 508. Starting from the estimate of the refractive index N, the computing means monitor the variations in the refractive index relative to a previous moment. The value of the refractive index at the previous moment can be drawn from the memory 508.

The foregoing description will be more easily understood by reference to FIG. 3 which is a simplified diagram illustrating the diffraction of the incident light beam 202 on the grating 50.

In short, the measuring means 57 supply a measurement of the angle of diffraction $\beta_p$ of the order p corresponding to a maximum intensity of the diffractive beam. The order p is determined by removing the ambiguity from the equation A1. It is known for example that the refractive index of pure water has been measured at:

$$1.43662 +/- 2.10^{-5},$$

for a wavelength of 193.3292 nm and a temperature of 21.50 degrees C. (NIST, National Institute of Standards and Technology). The computing means 505 then deduce from this the value of N, which is very precise either absolutely or only in its variations, as has already been seen.

It may be that prior knowledge of N does not enable one to remove the ambiguity as to p completely. Different solutions can then be envisaged. In particular, the measuring means 57 may be used to supply a measurement of two distinct diffraction angles $\beta_p$ and $\beta_k$ corresponding to intensity peaks of distinct orders of diffraction p and k, where p and k are integers. The simplest case is that of successive orders of diffraction (k=p+1).

The angle measuring means 57 may comprise a location sensitive photo-detector such as a fixed-position photo diode bar. The detection of a diffraction angle then takes place by the statistical treatment on the zone of the pixels that are illuminated by the diffracted beam on the photo diode bar. Other photo detectors may be used such as CCD sensors (charge coupled device), devices of the type known as PSD (position sensitive photodetector) or a pair of photo diodes differentially mounted to detect zero, for example.

Alternatively, the angle measuring means 57 may be mounted on a high precision goniometric arm.

In the remainder of the description the measuring means 57 will be of the high precision goniometric arm type, by way of example without being restrictive.

Figure 4:
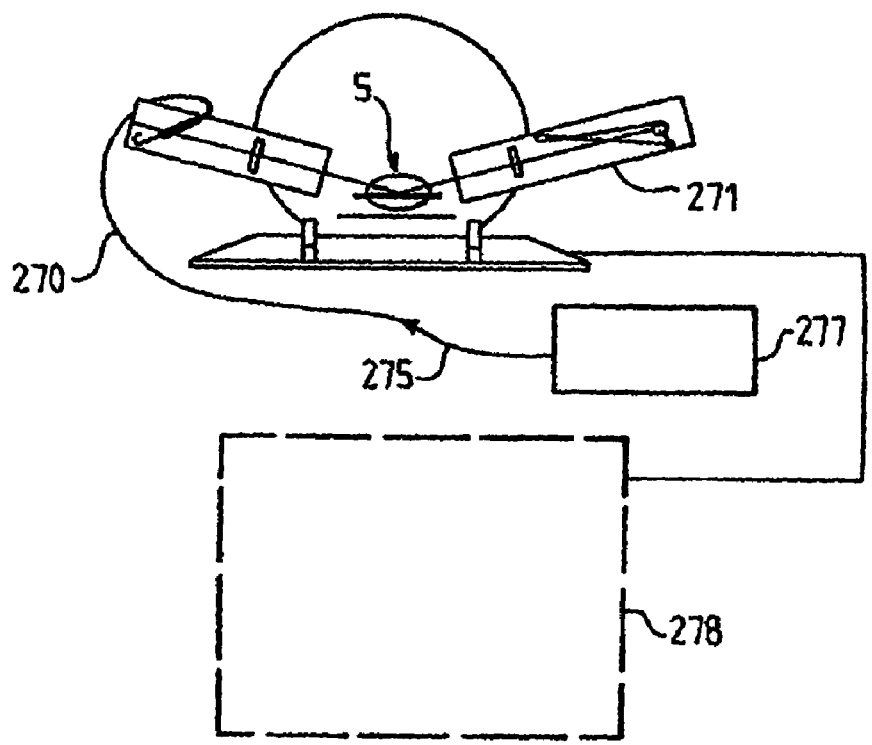
FIG. 4 is a diagram showing the angle measuring means.

Reference is made to FIG. 4, which shows an embodiment of a high precision goniometric system.

A goniometer of this kind comprises an analysing arm 270 and a source arm 271. In this embodiment the source 20 emits only the main beam 200. The source arm 271 constitutes the secondary source which emits the secondary beam 202 towards the grating 50. The optical axis of the source arm 271 defines the angle of incidence $\alpha$ of the incident secondary beam 202 on the grating.

In particular, the secondary light beam 202 consists of a monochromatic ray, for example the ray of the excimer laser, ArF which has a wavelength of the order of 193.3292 nm in a vacuum, or the atomic ray of the arsenic lamp which is at a wavelength of the order of 193.696 nm in a vacuum. The secondary source 20 may emit this monochromatic ray directly. Alternatively, the goniometer may be equipped with a spectrometer adapted to isolate a monochromatic ray of this kind from a polychromatic source.

The analysing arm 270 constitutes the arm for detecting the diffraction angles $\beta_p$. The detecting arm 270 and/or the source arm 271 may be movable during the measurement of the angles. After passing through the detecting arm 270, the diffracted beam 500 is focused on the entry to an optical fibre 275 providing an optical link with a detector 277. The detector may be a pixellated detecting surface, or a surface which may include a photomultiplier, and interacts with acquiring and processing means 278. In some cases it is also possible to use a spectrometer with a white light, which makes it possible to work at any desired wavelength.

The beam leaving the fibre 275 is focused on the entry to the detector. The detector produces a digital signal representing the light intensity of the diffraction spots. This signal is transmitted to the acquiring and processing means 278 which determine the intensity curve of the diffracted beam as a function of the diffraction angles.

The acquiring and processing means transmit, to the computing means 505 of the equipment 5, the diffraction angle $\beta_p$ corresponding to the intensity peak of the order of diffraction (p).

If appropriate, the computing means 505 will receive the couple of the diffraction angles $\beta_p$ and $\beta_{p+1}$ corresponding to the intensity peaks of the orders of diffraction (p) and (p+1), successive or otherwise. The computing means 505 take from this a value for the refractive index N according to the equations A1 and A2.

In addition, the source arm 271 of the goniometer may also provide a measurement of the angle of incidence $\alpha$ formed by the incident beam with the perpendicular CC to the grating 50.

The positioning of the arms 270 and 271 of the goniometer may also be regulated beforehand. To do this, the source arm 271 is initially positioned at 90°, by placing the centre of the spot on the edge of the grating 50. The source arm is then positioned at 0°. A check is then made to ensure that the alignment is correct, for example by an auto-collimation method. The source arm 271 is then positioned at the desired angle of incidence $\alpha$. The measurements using the detecting arm 270 can then begin.

Reference is again made to FIG. 2. The incident beam, emitted for example by the source arm 271, towards the grating, enters the chamber through the aperture 518 provided on a side wall 58 of the chamber 51. The beam diffracted by the grating leaves the chamber 51 through this same aperture 518.

For high precision it may be necessary to carry out prior calibration operations on the equipment 5.

The calibration may be carried out under reference conditions, with a reference liquid, which may be NIST standard pure water; its index has been measured at $$1.43662 +/- 2.10^{-5}$$

for a wavelength of 193.3292 nm and a temperature of 21.50° C. under a pressure of 1013 millibars.

Calibration may be carried out according to one or more of the following conditions:

of the air, on either side of the plate with parallel sides, so as to measure the effect of the plate on the output beam, as a function of the angle (it should be noted that this calibration is not absolutely necessary if the operator is chiefly interested in the variations in N to achieve a corrective feedback).

of the pure water upstream of the plate with parallel sides, and of the air downstream (upstream and downstream being in the direction of the outlet beam), to determine the effects inherent in the equipment for measuring the index with its diffraction grating and its goniometers.

if appropriate, calibration as a function of the temperature and/or pressure.

The equipment 5 according to the invention thus makes it possible to obtain an estimate of the refractive index of the liquid 3 with a high $\Delta N/N$ sensitivity, which may reach at least $0.5.10^{-6}$ and a $\Delta N$ of the order of $10^{-6}$. The word "estimate" is used here as a reminder that, at a given stage of lithography, the value of N cannot be known $\lambda$ in absolute terms; only its variations can be known with great precision and with high faithfulness or repeatability.

By contrast, when a number of lithographic systems are used in a coupled configuration (sequential and/or parallel arrangement) in the manufacture of a semiconductor device, it is often necessary to know the absolute value of N with the same precision as its variations so as to be able to "align" the mask images from one device to another. In fact, the magnification of the image of the mask on the chip must remain the same (at $\pm 10^{-6}$) regardless of the level of lithography on the same scanner or on different scanners.

The invention thus allows reliable monitoring of the variations in the refractive index as a function of a chosen parameter, for example the purity of the liquid, the wavelength $\lambda$, the temperature of the liquid, the pressure of the liquid (notably equal to $10^{-2}$ bars for water) or the time.

Additionally, the computing means 505 of the equipment 5 according to the invention may be adapted to calculate the coefficient of transmission T through the liquid from the light intensity of the diffracted beam.

The computing means may also be adapted to calculate the coefficient of absorption of the liquid from two estimates of the light intensity of the beam, one corresponding to a full chamber, the other to an empty chamber.

Additionally, the angle measuring means 57 may use a technique of digital adjustment to improve the precision of the magnitude relating to the refractive index.

The invention allows reliable and simple real-time monitoring, with a precision of the refractive index $\Delta N$ substantially greater than $10^{-6}$, and a sensitivity of the refractive index $\Delta N/N$ of the order of at least $0.5 \times 10^{-6}$, thus allowing rigorous monitoring of the variations in the refractive index. The monitoring device 6 can then adjust the parameters of the immersion liquid sufficiently early to prevent any significant degradation occurring in the images printed by the lithographic device 1. The monitoring process is carried out in particular at a faster rate than the variations, for example every 10 seconds.

The equipment according to the invention makes it possible to monitor the refractive index regardless of the wavelength $\lambda$ and independently of the index of the plate. These advantages, linked in particular with the use of a grating 50, are currently not achieved with the prism constructions of the prior art. In fact, a prism assembly would correspond roughly to p=1 in the formula A1. By contrast, using sufficiently high orders of diffraction, the proposed device makes it possible to increase the measuring sensitivity by adjusting the angle of incidence, and the diffracted order or orders p provided that (sin $\beta$) remains high enough, i.e. close enough to 1.

Thus, the applicant has determined that the sensitivity of the refractive index is increased by more than a factor 10 compared with these earlier embodiments. They have also observed that dN/N is inversely proportional to the tangent to the angle of incidence $\alpha$.

Of the parameters which may cause a variation in the refractive index, the temperature and the wavelength may be stabilised. In practice, notably in the field of immersion photolithography, it is particularly advantageous to stabilise the temperature of the liquid and/or the wavelength of the secondary light beam so as to detect the variations in the refractive index which have various other causes (for example the purity of the liquid). Hitherto the invention has been described with reference to a photolithographic application in which the temperature of the chamber 51 is stabilised.

However, as the causes of variations in the refractive index, other than the wavelength and temperature, are difficult to reproduce a priori, it may be useful, as an experiment, to vary the temperature of the liquid or the wavelength of the secondary beam, notably in order to check the performance of the invention in terms of sensitivity and precision and/or in order to make prior adjustments.

Figure 5:
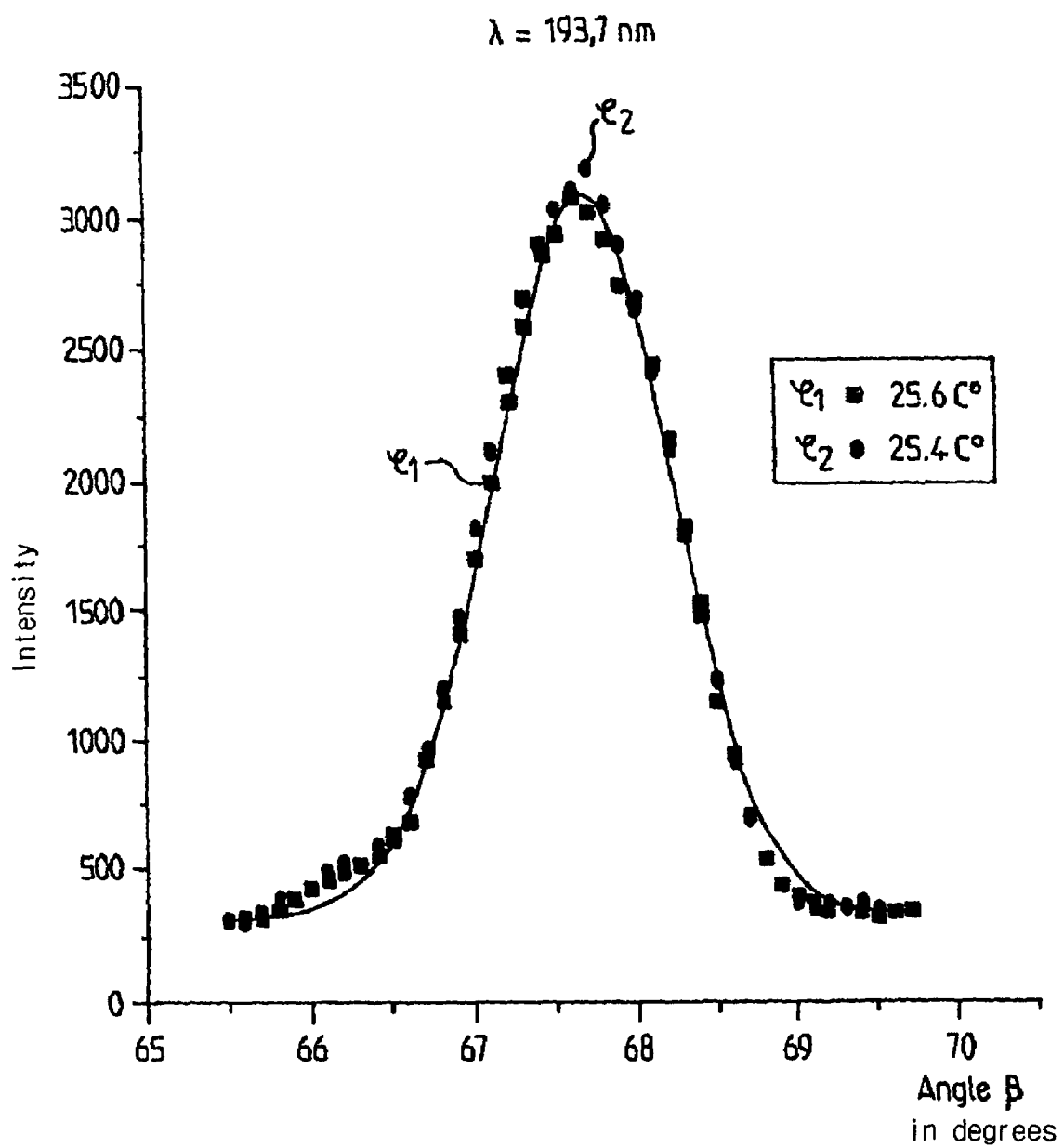
FIG. 5 is a diagram showing the variations in the diffraction intensity as a function of the observation angle, for two different temperatures of the liquid.
Figure 6:
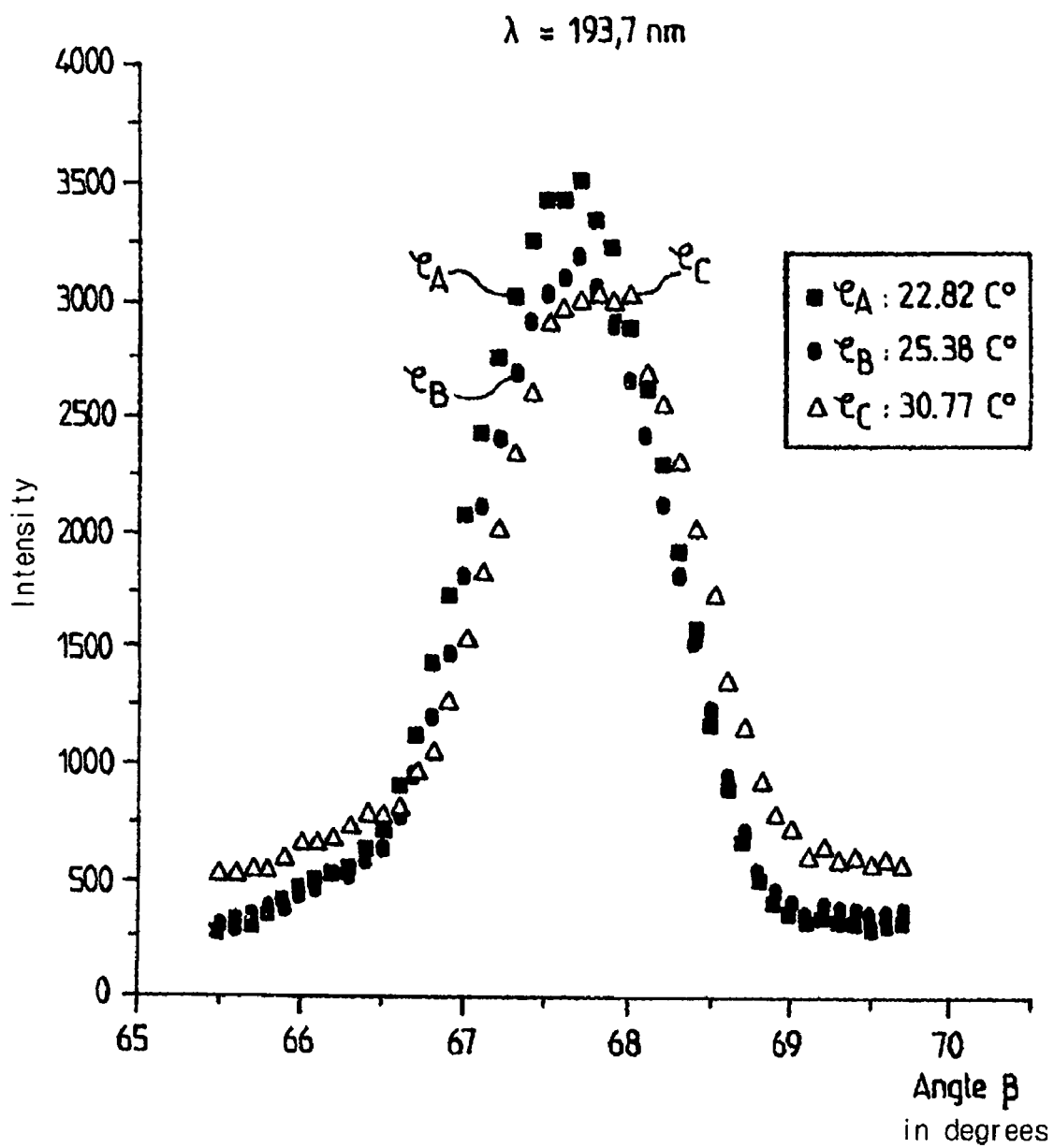
FIG. 6 is a diagram representing the variations in the diffraction intensity as a function of the observation angle, for three different temperatures of the liquid.
Figure 7:
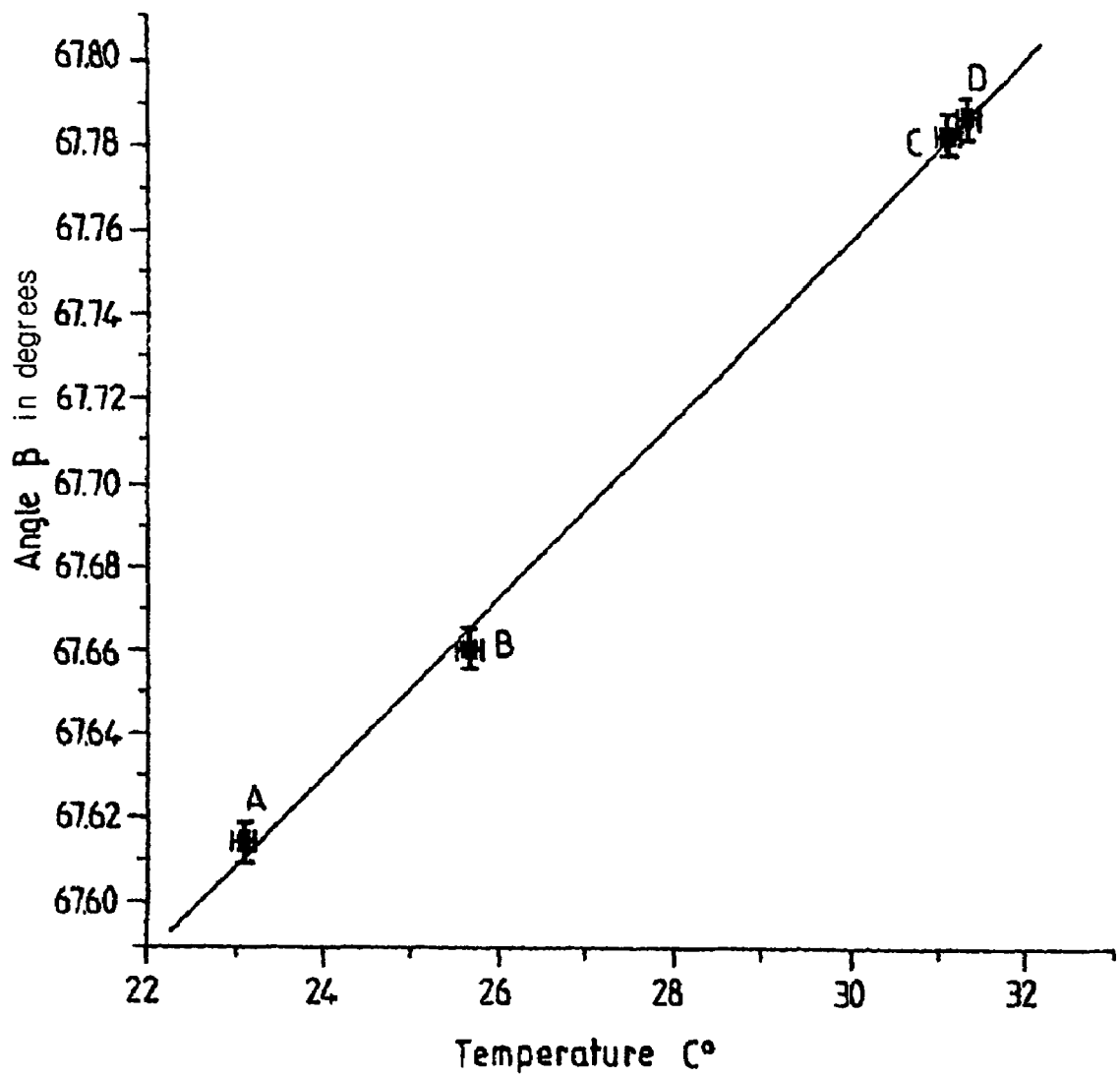
FIG. 7 is a diagram showing the variations in the diffraction angle as a function of temperature.

FIGS. 5 to 7 correspond to embodiments of the invention in which the temperature of the liquid varies.

More precisely, FIG. 5 is a diagram showing the variation in the intensity diffracted as function of the observation angle $\beta$ for a wavelength of 193.7 nanometers. Two Gaussian curves are shown. The curve C1 shown by small squares corresponds to a liquid temperature of 25.4° C. and the curve C2 represented by dots corresponds to a liquid temperature of 25.6° C.

Observation of these two Gaussian curves C1 and C2 shows that, for a temperature variation of 0.02° C., an angular offset of about 0.04° is obtained.

As such an offset is at the limits of precision of the angle measuring instrument used, the experiment carried out here demonstrates the repeatability acquired for the operation of the proposed device.

When carried out with greater temperature offsets, the same experiment can be used to estimate the angular offset as a function of the temperature, thus FIG. 6 is a diagram showing three curves $C_A$, $C_B$, and $C_C$ representing the variations in the observation angle $\beta$ corresponding respectively to temperature values of 22.82° C., 23.58° C. and 30.77° C.

FIG. 7, which shows the variations in the observation angle $\beta$ as a function of temperature, shows three points A, B and C which correspond respectively to the curves $C_A$, $C_B$, and $C_C$ in FIG. 6. Another point D shown in FIG. 7 is not shown in FIG. 6, in the interests of clarity.

From the Gaussian curves $C_A$, $C_B$, and $C_C$, it is also possible to deduce vertical confidence limits, as shown in FIG. 7. Linear regression carried out on the points A, B and C gives a straight line with a slope of about 0.213 angular degrees per degree Celsius.

It is also known (NIST experiment) that the variation in the refractive index N for the medium under consideration is $-10^{-4}$ per degree Celsius.

The sensitivity of the angular measurements is 5 thousandths of an angular degree, corresponding to 0.23° C. This gives a variation of $2.3 \times 10^{-5}$ for the refractive index N.

Moreover, in terms of order of magnitude, under reference conditions, in terms of pressure and hygrometric degrees, the measurements by the applicant have yielded the following values:

N=1.43612, for a wavelength of 193.696 nanometers and a temperature of 23° C.; and N=1.43532 for a wavelength of 193.696 nanometers and a temperature of 31° C.

Moreover it may be useful to carry out the monitoring process of the invention by operating at different wavelengths, or at a number of wavelengths, particularly within an experimental framework.

Figure 8:
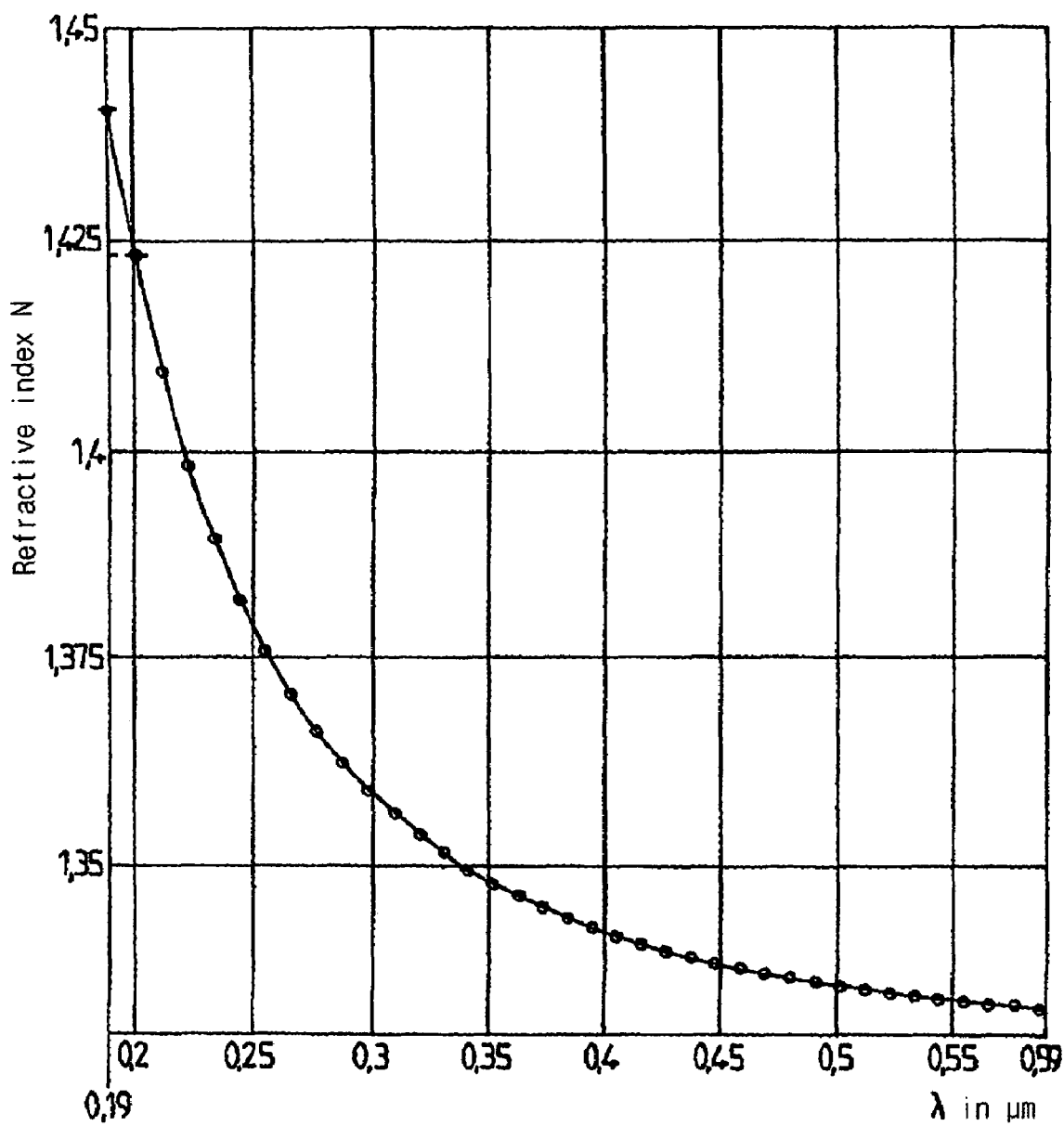
FIG. 8 is a diagram showing the variations in the refractive index as a function of the wavelengths.

FIG. 8 is a diagram showing the variations in the refractive index N of pure water as a function of the emission wavelength, for a temperature of 23° C.

This figure shows that the sensitivity of the variation in index as a function of the wavelength is high at around 0.2 micrometers, i.e. 200 nanometers.

The invention has been described with reference to a reflection-type diffraction grating, as a non-restrictive example. Alternatively, the equipment according to the invention may use a transmission-type diffraction grating. Such a grating may be processed by engraving and consist of alumina. It is chosen so as to have a refractive index greater than 2. Thus a gain in resolution may be obtained (index of the grating over the index of the liquid), a gain in stability and a gain by transmission in the liquid compared with the reflection grating described above.

Although the equipment according to the invention is particularly advantageous for in situ monitoring of a lithographic device, it may be used in other types of optical applications. For example, it may be used in the laboratory and/or in high precision liquid chromatography and detection, without any direct interaction with a lithographic device, in order to carry out precise measurements of the refractive index of a liquid, or a magnitude representing this index, or connected therewith.

More generally, the invention provides a device for highly accurate in situ measurement of the refractive index of a liquid, which could be used as it is.

The invention has been described with reference to an optical focusing device 53 of the collimating mirror type. However, other types of optical equipment may be used, especially diopter devices.

It has been seen that the embodiment of the window 56 in the form of a plate with parallel sides gives rise to certain simplifications. However, this window 56 may also take other forms such as a prism, particularly a thin prism.

When the angle of incidence α varies, instead of being fixed, a separate detector may be used to measure it.

ANNEXE A $$\sin(\alpha) + \sin(\beta_p) = \frac{pg\lambda}{N} \quad \text{A1)}$$

$$\sin(\alpha) + \sin(\beta_{p+1}) = \frac{(p+1)g\lambda}{N} \quad \text{A2)}$$

$$\sin(\beta_{p+1}) - \sin(\beta_p) = \frac{g\lambda}{N} \quad \text{A3)}$$

$$n_{liq} \sin i_{liq} = n_{plate} \sin i_{plate} = n_{air} \sin i_{air} \quad \text{A4)}$$

The invention claimed is:

1. Equipment for monitoring an immersion lithographic device equipped with a main light source (20) and an optical projection device (25) for printing images on a chip (4), the propagation medium going from the optical projection device to the chip consisting of a liquid (3), characterised in that it comprises:
    a chamber (51), adapted to receive at least some of said liquid (3),
    a diffraction grating (50) immersed in the chamber,
    a secondary light source (271) adapted to send a secondary incident beam (202) towards the grating so as to obtain a diffracted beam,
    angle measuring means (57) capable of measuring at least one diffraction angle corresponding to an intensity peak of an order of diffraction of the beam diffracted by the grating (500), and
    computing means (505) adapted to calculate an estimate of a magnitude relating to the refractive index of the liquid.

2. Equipment according to claim 1, characterised in that the measuring means (57) are furthermore adapted to measure another diffraction angle corresponding to the intensity peak of another order of diffraction, different from the first.

3. Equipment according to claim 1, characterised in that the magnitude relative to the refractive index is the refractive index of the liquid itself.

4. Equipment according to claim 1, characterised in that the magnitude relating to the refractive index is the variation in the refractive index of the liquid.

5. Equipment according to claim 1, characterised in that the secondary light beam (202) consists of a monochromatic ray.

6. Equipment according to claim 1, characterised in that the chamber (51) has a lateral separating wall (58) comprising an aperture (518), through which the incident beam (202) directed onto the grating (50) and the beam (500) diffracted by the grating pass.

7. Equipment according to claim 6, characterised in that the aperture is closed off by a window (56) that separates the chamber (51) from the outer medium.

8. Equipment according to claim 7, characterised in that the window is a plate of silica.

9. Equipment according to claim 1, characterised in that the window (56) is a plate with parallel sides.

10. Equipment according to one claim 1, characterised in that the chamber (51) comprises temperature control means (60) suitable for maintaining a selected temperature in the chamber.

11. Equipment according to claim 10, characterised in that the stability of the temperature chosen is of the order $10^{-2\circ}$ C.

12. Equipment according to claim 1, characterised in that it comprises an optical device (53) for focusing the diffracted light beam on said measuring means (57).

13. Equipment according to claim 12, characterised in that the optical device (53) comprises a collimating mirror.

14. Equipment according to claim 1, characterised in that the angle measuring means (57) comprise a position sensitive photo-detector arranged so as to receive the light beam refracted by the grating (50).

15. Equipment according to claim 1, characterised in that the secondary source comprises means for taking some of the beam emitted by said main source (20) in order to form the secondary light source (202).

16. Equipment according to claim 1, characterised in that the angle measuring means (57) comprise a goniometer equipped with a detecting arm (270) and a source arm (271).

17. Equipment according to claim 16, characterised in that the source arm (271) of the goniometer constitutes the secondary light source.

18. Equipment according to claim 1, characterised in that the measuring means (57) are also adapted to measure the angle of incidence of the secondary beam (202).

19. Method of monitoring a lithographic device equipped with a main light source (20) and an optical projection device (22) for printing images on a chip (4), the propagating medium which goes from the optical projecting device to the chip consisting of a liquid (3), characterised in that it comprises the following steps:
    a) providing a chamber (51) that receives at least some of said liquid (3),
    b) sending a secondary incident beam (202) towards a diffraction grating immersed in the chamber,
    c) measuring at least one diffraction angle corresponding to an intensity peak of at least one order of diffraction of the beam diffracted by the grating (500) and
    d) calculating an estimate of a magnitude relating to the refractive index of the liquid.

* * * * *